United States Patent [19]
Davey et al.

[11] Patent Number: 5,332,401
[45] Date of Patent: Jul. 26, 1994

[54] APPARATUS AND METHOD FOR TRANSCRANIAL ELECTROTHERAPHY

[76] Inventors: Ronald W. Davey, 1 Upper Wimpole Street, London, W1M 7TD; Ifor D. Capel, Ty Derw, 53 Chaldon Common Road, Chaldon, Surrey, CR 3, both of Great Britain

[21] Appl. No.: 859,478
[22] PCT Filed: Oct. 31, 1990
[86] PCT No.: PCT/GB90/01670
 § 371 Date: Jun. 15, 1992
 § 102(e) Date: Jun. 15, 1992
[87] PCT Pub. No.: WO91/06340
 PCT Pub. Date: May 16, 1991

[30] Foreign Application Priority Data
 Nov. 1, 1989 [GB] United Kingdom ............. 8924559.1

[51] Int. Cl.5 .......................... A61N 1/05; A61N 1/36
[52] U.S. Cl. ........................ 607/116; 607/46; 607/58; 607/74; 607/139; 607/149; 607/900
[58] Field of Search ............ 128/784, 785, 789, 791, 128/802, 419 S, 421, 422, 907; 606/204; 607/46, 58, 72, 74, 76, 116, 139, 149, 900

[56] References Cited
U.S. PATENT DOCUMENTS
3,957,053 5/1976 Woo ................... 128/907 X
4,319,584 3/1982 McCall ..................... 128/789

FOREIGN PATENT DOCUMENTS
22029 10/1961 German Democratic
 Rep. ........................ 128/784
764686 9/1980 U.S.S.R. ................... 128/789
1169653 7/1985 U.S.S.R. ................... 606/204

Primary Examiner—Lee S. Cohen
Attorney, Agent, or Firm—Ostrolenk, Faber, Gerb & Soffen

[57] ABSTRACT

An electrode for providing TCET, especially via the earlobes of the patient, comprises an electrical conductor for application to the skin, connected to a lead for supplying the TCET signal from a signal generating device, characterized in that the conductor comprises a generally conical needle point capable of penetrating the epidermis so as to provide good electrical contact over a very small area. The electrode can be used in the impedance of less than 100 kΩ; and with apparatus for generating an electrical signal for use in TCET, adapted to provide a signal at a current of less than 200 μA (0.2 mA), especially when adapted to provide an AC signal in which each positive pulse is relatively short and high without being spiked and the following negative pulse is relatively wide and low, the total amount of positive and negative charge being balanced. Methods of providing TCET treatment to patients using the electrode and apparatus are also provided.

14 Claims, 5 Drawing Sheets

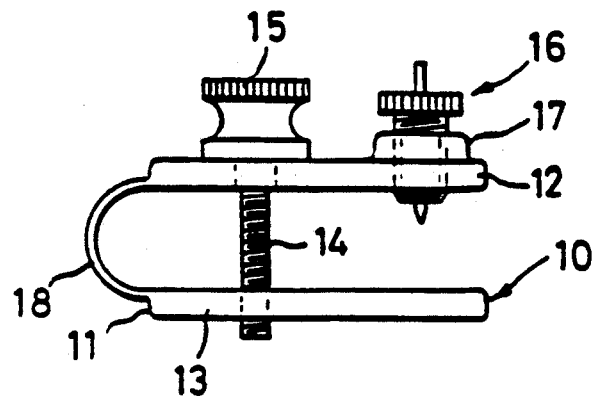
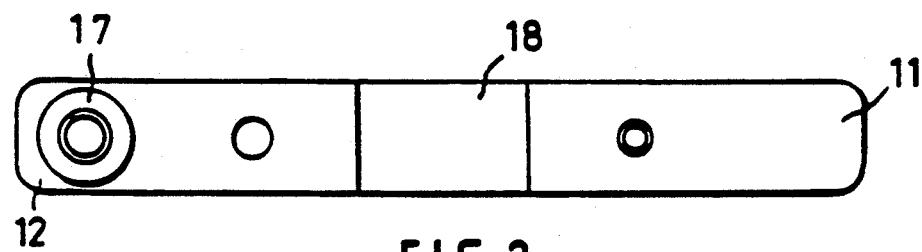
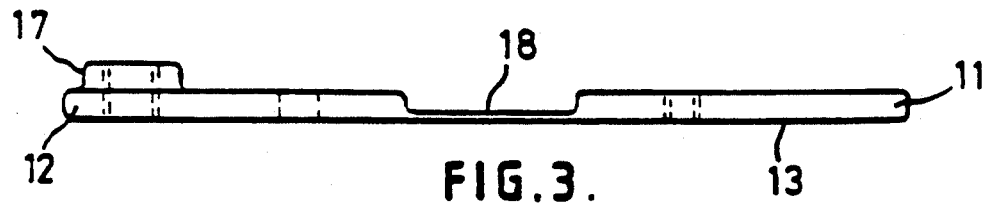
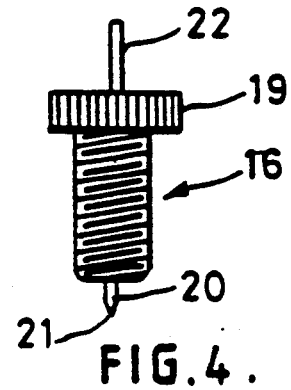

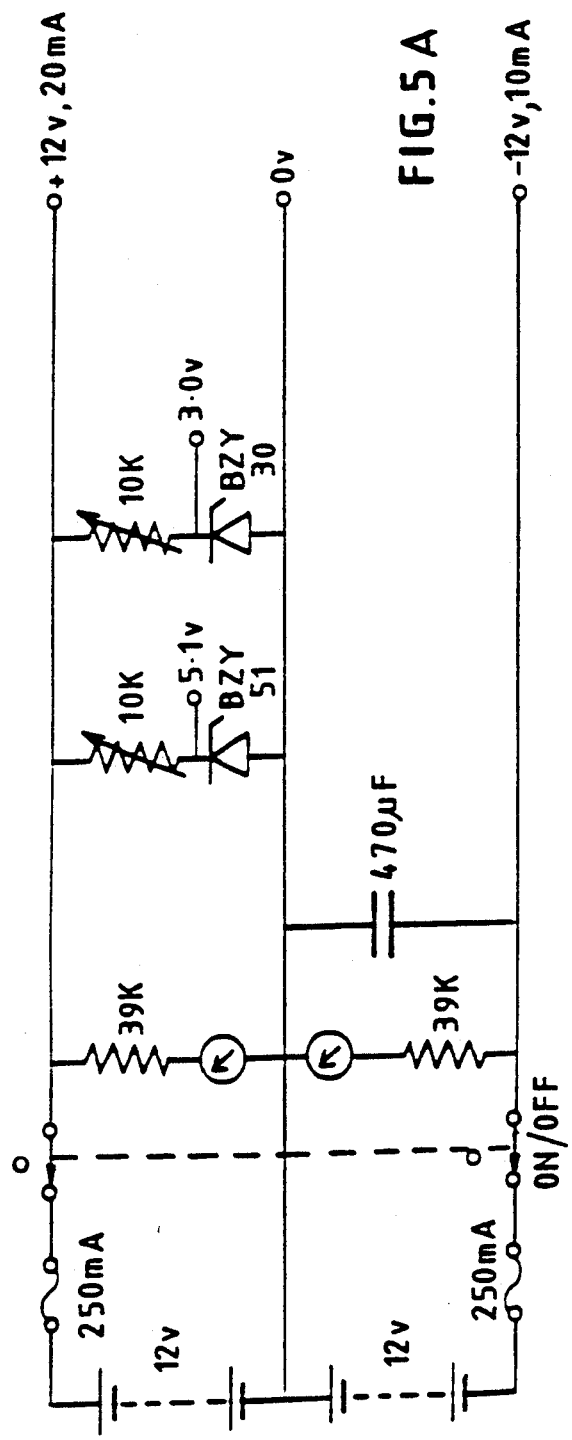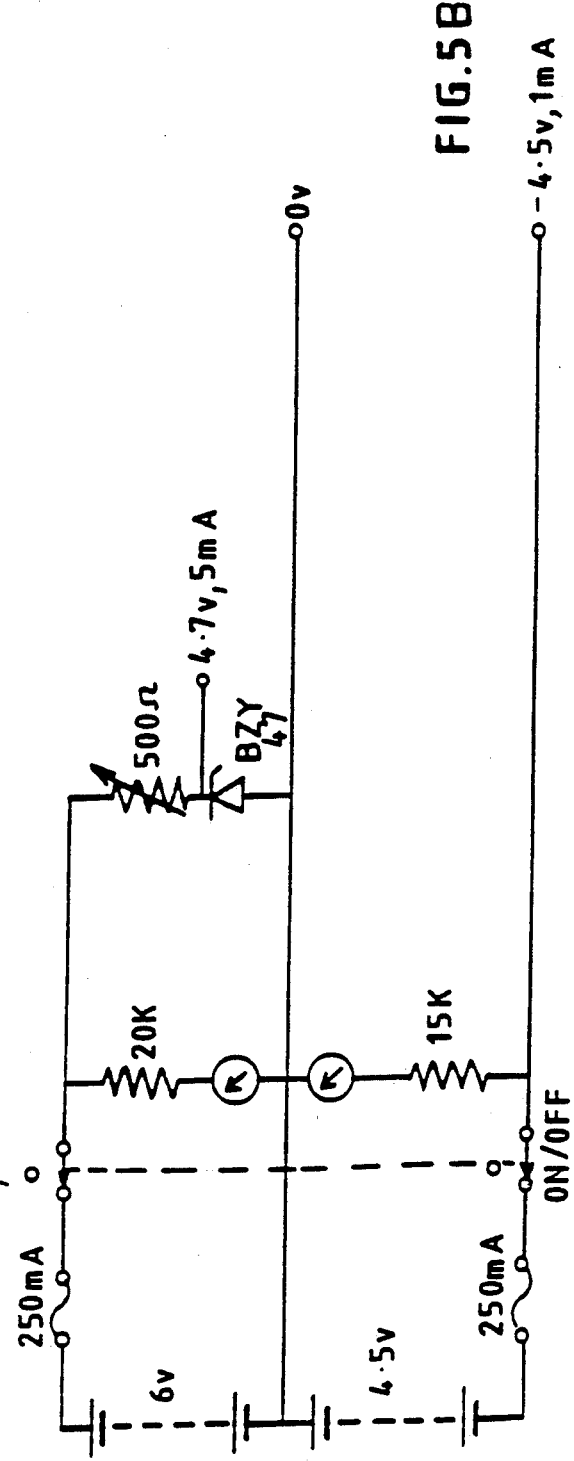

APPARATUS AND METHOD FOR TRANSCRANIAL ELECTROTHERAPHY

BACKGROUND OF THE INVENTION

This invention relates to the process now known as TCET (transcranial electrotherapy), that is to say the application of a series of electric signals of defined amplitude and duration across the head of a patient or a test animal by means of percutaneous electrodes generally attached to the external part of the ear.

TCET is described in detail in U.S. Pat. No. 4 646 744 issued Mar. 3, 1987. The U.S. patent describes the general concept of TCET and distinguishes it from other known methods, in particular TENS (Trans cutaneous Electrical Nerve Stimulation), electro-acupuncture and invasive electrical treatment. TCET is particularly important in the control of chronic refractory pain, but is also important in treatment of addictive states.

We have now found that for TCET to be successful a number of factors must be considered and the application of the electrical signals must be carried out in a precisely defined manner using signals having particular parameters. It is thus the object of the present invention to provide a method of applying TCET which is effective and reproducible.

U.S. Pat. No. 4 646 744 discloses the application of a signal comprising trains of pulses separated from other trains by off periods. Each of these trains comprises a packet of a certain number of individual pulses spaced temporally from other packets by off periods. The pulses are generally either DC or substantially symmetrical AC wave forms applied at a number of different frequencies, typically 10 Hz, 100 Hz, 25-30 Hz, 500 Hz, and 200 Hz. The pulse width, that is to say the duration of a positive pulse from a zero value to a zero value, is typically 0.1 to 0.5 msec, although pulse widths of 1.5 msec are also mentioned. As described, the signals have a current of several mA, and an amperage of less than 100 mA being sufficient.

As stated, the pulses are given in packets of consecutive pulses described as "trains" separated by off periods which can regularly spaced or which can be irregular and typically increasing in duration, e.g. in an arithmetical progression. The typical overall duration of these series of trains is several days.

SUMMARY OF THE INVENTION

We have now established that there are a number of important parameters to supply if the treatment is to be effective and reproducible. In the first place it is important to consider the impedance of the circuit, as controlled by the electrode attachment to the ear. We have now found that conventional patch electrodes, even if relatively small for accurate placement, as advised in the above-mentioned U.S. patent, provide a relatively high impedance, typically 300–600 kΩ, even when used with electrode gel, and also a relatively large capacitance. Similarly, a blunt gold electrode has an impedance of 300–500 kΩ. I have found that the electrode should be in the form of a generally conical needle point capable of penetrating the epidermis, so as to provide good electrical contact over a very small surface area. A steel needle electrode of this type provides an impedance of about 65–90 kΩ, whale a carbon needle provides an impedance of about 25–35 kΩ. The point contact also provides a low capacitance.

BRIEF DESCRIPTION OF THE DRAWINGS

FIG. 1 is a side view of an electrode assembly;

FIGS. 2 and 3 are plan and side views of the assembly before being folded;

FIG. 4 is a large side view of the electrode carrier of the assembly;

FIGS. 5A and 5B, 6 and 7 show a power supply circuit and signal generator.

DESCRIPTION OF THE INVENTION

Figure 6:
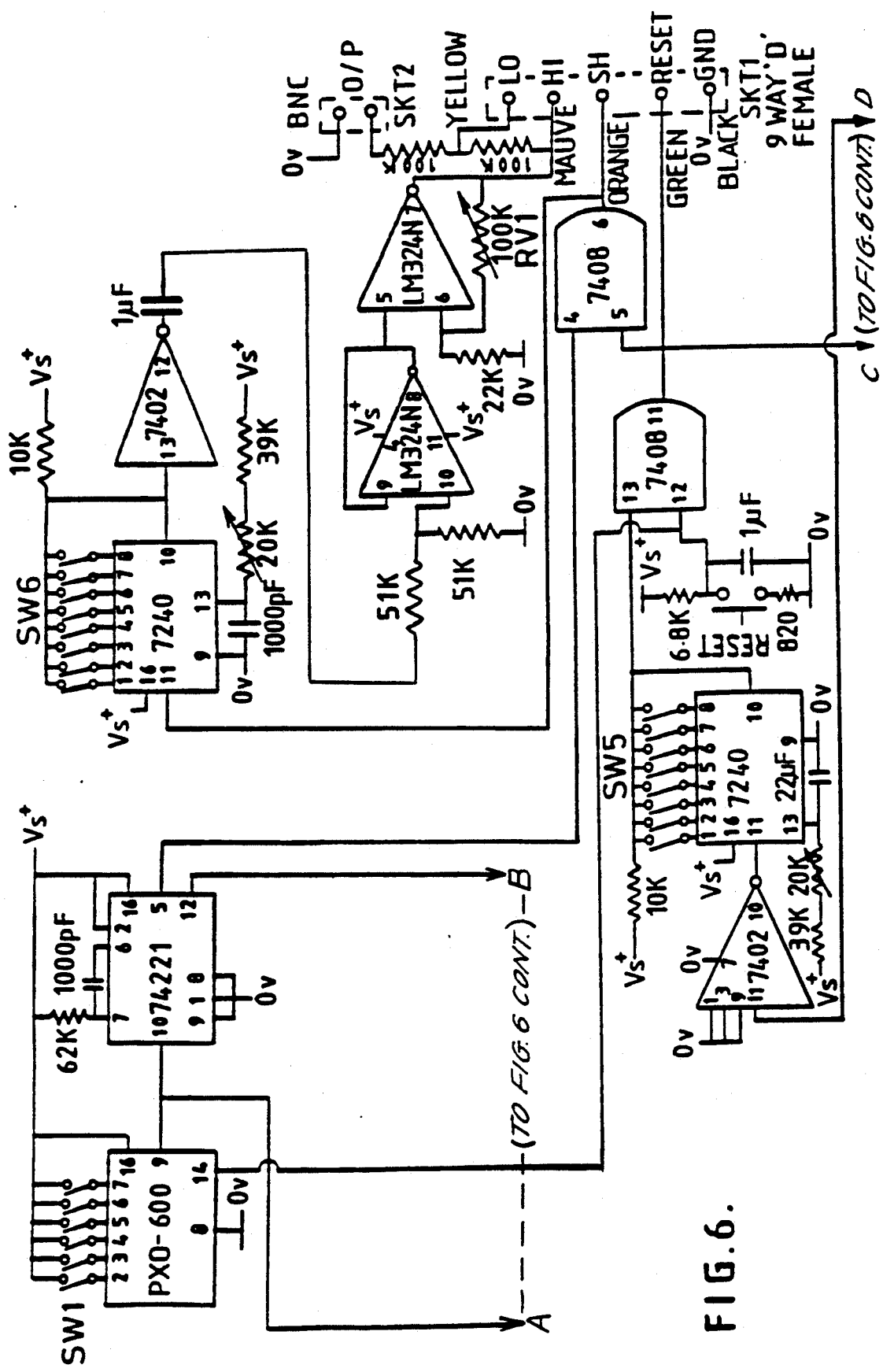
Figure 6:
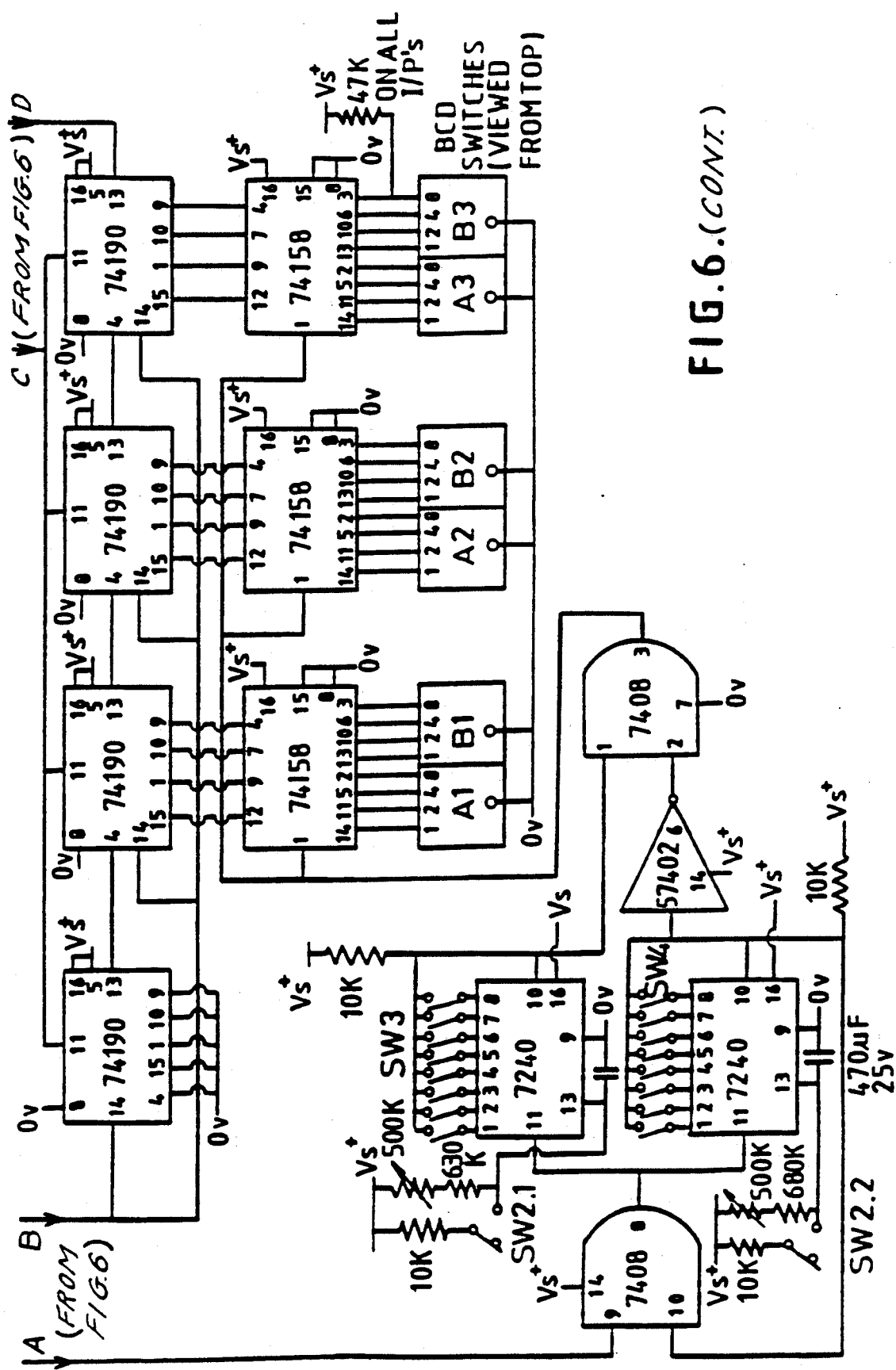

The signal can be provided to the electrode with a very low current. It is highly desirable to use an operating current of only a few microamps, typically 10–15 $\mu A$ e.g. about 10–12 $\mu A$. Thus, the operating current should be a factor of $10^{-4}$ times the operating current suggested in the above-mentioned U.S. patent.

The low current signal can be provided by the simple procedure of using a signal generator working at a much higher current and then including in the circuit a defined high impedance to reduce the current to the required microamp levels. Typically a signal is generated at from 2-4 volts and passed through a 180 k$\Omega$ resistance.

It is also most important that the connecting leads are kept as short as possible, or are screened (if this is feasible). Long unscreened leads (or, even worse, long screened but non-earthed leads) are found to act as aerials and pick up a large amount of ambient electromagnetic radiation, thus delivering to the patient a large amount of "noise" along with the signal. This is at best unhelpful, and at worst positively harmful, apparently causing aggressive tendencies in rats and irritation or anxiety in humans.

Another particularly preferred aspect of the invention, comprises an electrode in the form of an ear clip, generally comprising a bifurcated or generally U-shaped holder capable of being located around the ear lobe and supplied with a conically pointed electrode needle arranged to press against the ear lobe located between arms of the U-shaped clip, the electrode being provided with adjustable means for controlling the pressure at which the point of the electrode presses into the outer layers of the skin; the electrode also being provided with an electrical connection to the signal generator. The clip is conveniently made of molded plastic material, for example nylon or polyalkylene. The adjustable means for controlling the pressure is conveniently a transversely mounted screw device controlled by, for example, a knurled knob and the electrode is conveniently attached to the lead by a conventional crimped ferrule.

A further important operating condition is that the overall net charge delivered to the patient should effectively total zero (i.e. the positive charge should balance the negative charge in an alternating current), but that the operating signal should effectively consist of pulses of positive current. This result can be achieved by using an AC waveform in which the positive pulse is relatively short and high, while the following negative pulse is relatively long and low, the "areas" of the pulses being equal. (This description refers to the conventional representation of pulses as voltage plotted against time). Typically, the positive pulse should have a duration of about 2-2.2 msec (although pulse width of 0.22 msec and 7 msec are also effective in some cases) and the negative pulse width should be 5-10 times as long e.g. about 7 times. The pulse width (pulse duration)

must obviously be less than the reciprocal of the frequency and we find that for frequencies up to, say, 150 Hz a pulse width of 2.0 msec is optimal, while at a frequency of about 500 Hz a pulse width of l msec is optimal and at a frequency of about 2000 Hz a pulse width of less than 0.1 msec is optimal. If it is desired to use ultra high frequency (MHz) signals, the pulse width is undefined. It is also important that the positive pulse is not significantly "spiked" at its onset, contrary to the teaching of U.S. Pat. No. 4,646,744.

As a further preferred feature of this invention it is generally undesirable for the sequence of packets of pulses (previously referred to as "trains") to be continued for days without longer breaks. We have now found that the signal should be supplied as packets of pulses separated by short pauses in a relatively short sequence which can, more realistically, be referred to as a "train". The trains themselves are then separated by longer breaks.

At the particularly preferred frequency of 10 Hz, we have found that a typical train should contain packets of 750 or 1000 individual pulses, i.e. packets of 75 or 100 seconds in duration, separated by pauses of about 10 seconds, for a total train duration of 1800–3600 seconds, e.g. 2400 seconds. The rest period between successive trains of this type should preferably be a minimum of 3 hours. We have found that this type of signal provides distinctly better results than either continuous operation or operation involving a series of packets and gaps continued for several days.

In a further preferred aspect, the invention includes apparatus for generating the appropriate signal, as described above.

Such apparatus may conveniently comprise any suitable electronic circuitry capable of providing an appropriate electrical signal e.g. that described in the above-mentioned U.S. patent. In a preferred embodiment, it comprises digital analog circuitry to gate the signals into the required conformation.

Subjects receiving specific prescriptions, including the 250 and 750 ppp delivered at 10 Hz find that their mouths become dry during treatment sessions of one hour duration. Furthermore, alcoholics receiving treatment To ameliorate the abstinence symptoms associated with the withdrawal of alcohol become dry mouthed and also exhibit pronounced hypoglycaemic responses. However, it is undesirable to let the patient drink during the treatment period, as tests are carried out on the saliva, which would be diluted by the water etc. It is now therefore recommended that the recipients of the treatment suck commercially available glucose tablets (generally containing approx. 3 g of the monosaccharide) as a salivation stimulant. One tablet is administered 15–20 min before commencement of therapy and thereafter at 30 min intervals upon the discretion of the supervising clinician.

In summary, therefore, we now provide a modified version of the method described in the U.S. Patent, utilizing a combination of parameters selected from those described above, which enable for the first time the method to be applied in a scientifically reproducible, effective manner, especially for pain control. A convenient electrode clip for attachment to the ear is also provided. There is also provided signal generating apparatus for providing the type of signal train described.

The following description is by way of exemplification of various aspects of the invention.

The relevance of a number of different treatment parameters was evaluated in rats using a signal of 10 Hz at 2–4 volts. Analgesic effect was measured by measuring the tail flick latency (TFL) in rats using a conductive heat challenge in the standard way. Further indication of activity is provided by measurement of $\beta$-endorphin (BE) levels, adrenocorticotrophic hormone (ACTH) levels and also the levels of corticosterone and cortisol. The estimation of these levels is carried out by measuring their immunoreactivity ($-$Ir) using an immunological technique using radio labelled antigen (referred to as It). The details of the electrical stimulation (ES) are as stated in the footnotes to each table.

TABLE 1

TFL in rats receiving continuous mode ES of various current amplitudes.

| Current Amplitude ($\mu$A) | TFL (s) |
| --- | --- |
| 420 | 13.4 ± 6.5* |
| 330 | 17.0 ± 4.2* |
| 250 | 20.0 ± 6.2 |
| 180 | 27.3 ± 2.6* |
| 80 | 27.0 ± 3.2* |
| 20 | 26.0 ± 3.4* |
| 15 | 35.2 ± 7.2* |
| 10 | 32.2 ± 8.1* |
| 5 | 32.0 ± 6.6* |
| 1 | 28.1 ± 5.0* |
| 0.5 | 24.6 ± 10.0 |
| 0.2 | 21.4 ± 8.8 |
| 0.1 | 22.4 ± 6.5 |
| 0.05 | 21.4 ± 10.1 |
| Sham-treated | 21.3 ± 5.0 |

Results are the mean ±SD of 6 rats in each group. Continuous mode ES administered at 10 Hz frequency 2.0 Oms pulse width for a period of 1800 s. Noxious challenge: TFL determined with conductive heat challenge at 60° C. applied to the ventral surface.

* Significantly different (P<0.05) from sham-treated value by unpaired Student's t test.

TABLE 2

Effect of varying the pause duration Dp (time off) and stimulation period (time on) on the antinociceptive action of interrupted mode ES in the TFL.

| Dp (s) | TFL (s) |
| --- | --- |
| 100 | 18.4 ± 7.8* |
| 50 | 18.2 ± 8.6* |
| 20 | 15.2 ± 6.0 |
| 10 | 28.1 ± 7.0* |
| 5 | 20.5 ± 11.8* |
| 2 | 17.7 ± 7.3 |

| Time on (s) | TFL (s) |
| --- | --- |
| 5 | 9.1 ± 3.4* |
| 25 | 28.1 ± 7.0* |
| 50 | 30.6 ± 6.2* |
| 75 | 33.8 ± 7.4* |
| 100 | 35.4 ± 6.1* |
| 150 | 24.0 ± 5.0* |
| 200 | 23.8 ± 4.2* |
| 250 | 22.1 ± 5.4* |
| Sham-Treated | 14.4 ± 6.4 |

Results are the mean ±SD of 18 rats in each group.

For determination of optimum pause: ES consisted of 25 s periods of stimulation separated by the pause periods indicated and administered for a total treatment time of 1800 s. Sham-treated animals were restrained for the corresponding period of time with electrodes inserted but no current was passed.

Noxious challenge: TFL determined with conductive heat challenge at 60° C. applied to the ventral surface.

* Significantly different (P<0.05) from sham-treated value by unpaired Student's t test.

TABLE 3

Effect of varying the signal pulse width on the antinociceptive action of interrupted mode ES in the TFL.

| Pulse width (ms) | TFL (s) |
|---|---|
| 1.8 | 19.1 ± 2.1* |
| 1.9 | 16.9 ± 7.8* |
| 2.0 | 28.4 ± 5.5* |
| 2.1 | 31.4 ± 8.2* |
| 2.2 | 29.0 ± 6.1* |
| 2.4 | 19.0 ± 7.1* |
| 2.6 | 17.4 ± 9.1 |
| Sham-treated | 14.2 ± 6.5 |

Results are the mean ±SD of 12 rats in each group. ES consisted of periods of 100 s stimulation separated by 10s pause periods administered for a total treatment time of 1800 s. Sham-treated animals were restrained for the corresponding period of time with electrodes inserted but no current was passed.

Noxious challenge: TFL determined with conductive heat challenge at 60° C. applied to the ventral surface.

* Significantly different (P<0.05) from sham-treated value by unpaired Student's t test.

TABLE 4

Effect of varying the current amplitude on the antinociceptive action of interrupted mode ES in the TFL.

| Current Amplitude (μA) | TFL (s) |
|---|---|
| 33.0 | 15.6 ± 7.5 |
| 20.0 | 23.4 ± 9.9* |
| 18.0 | 19.7 ± 7.6* |
| 12.5 | 31.8 ± 7.0* |
| 11.0 | 32.2 ± 5.2* |
| 10.0 | 26.4 ± 7.0* |
| 9.5 | 14.6 ± 3.7 |
| 5.0 | 13.4 ± 3.1 |
| Sham-treated | 14.2 ± 6.5 |

Results are the mean ±SD of 12 rats in each treatment group.

Interrupted mode ES of 2.0 ms pulse width signals at the current amplitude indicated, consisted of periods of 100s stimulation separated by 10s pause periods administered for a total treatment time of 1800 s. Sham-treated animals were restrained for the corresponding period of time with electrodes inserted but no current was passed.

Noxious challenge: TFL determined with conductive heat challenge at 60° C. applied to the ventral surface.

* Significantly different (P<0.05) from sham-treated value by unpaired Student's t test.

TABLE 5

Comparison of the antinociceptive effects of interrupted, continuous mode ES and sham treatment.

| Treatment Group | TFL |
|---|---|
| Interrupted | 30.8 ± 7.4* (18) |
| Continuous | 18.3 ± 11.5* (18) |
| Sham-treatment | 14.3 ± 6.4 (19) |
| Basal | 10.8 ± 5.3* (16) |

Results (in s) are the mean ±SD for numbers of rats in parentheses.

Rats received a 1800 s treatment period of one of either: Interrupted mode ES of 100s of stimulation separated by 10 s pause periods when the current was off; continuous mode ES identical in all respects to interrupted except devoid of pauses; Sham-treatment (electrodes inserted but no current passed); Basal rats restrained briefly (<300s) for noxious challenge in TFL.

Noxious challenges: TFL determined with conductive heat challenge at 60° C. applied at the ventral surface.

* Significantly different (P<0.05) from sham-treated value by unpaired Student's t test.

TABLE 6

Plasma concentrations of BE, ACTH, corticosterone (c/one), cortisol (c/ol) and SP-Ir in rats receiving interrupted, continuous mode ES or sham-treatment.

| Treatment Group | BE-Ir (pg/ml) | ACTH-Ir (pg/ml) | c/one-Ir (ng/ml) | c/ol-Ir (ng/ml) |
|---|---|---|---|---|
| Interrupted | 215 ± 90** (12) | 373 ± 25** (6) | 1023 ± 76** (6) | 22 ± 15** (12) |
| Continuous | 187 ± 66 (14) | 778 ± 397 (8) | 994 ± 266** (8) | 20 ± 4** (6) |
| Sham-Treated | 163 ± 76 (14) | 978 ± 250** (8) | 900 ± 160** (8) | 18 ± 6** (18) |
| Basal | 145 ± 80 (14) | 531 ± 244* (8) | 499 ± 165* (8) | 14 ± 6* (6) |

Results are the mean ±SD for numbers of rats given in parentheses.

Rats received a 1800 s treatment period of one of either: Interrupted mode ES of 100s of current separated by 10s pause periods ( current off), pulse width 2.0ms; Continuous mode ES identical in all respects to interrupted, except devoid of pauses; Sham-treated (with electrodes inserted but no current passed); Basal rats were killed after brief restraint (<300s) for antinociceptive testing by the TFL test. TFL determined with conductive heat challenge at 60° C. applied to the ventral surface after which the rats were killed and the blood collected.

* Significantly different (P<0.05) from sham-treated value by unpaired Student's t test.

** Significantly different (P<0.05) from basal value by unpaired Student's t test.

Comparison of impedance values with differing electrodes

Examples of electrodes applied at the ear lobes

Sharp needles which penetrate the epidermis:
(a) steel needles 77 kΩ±11 kΩ
(b) carbon needles 30 kΩ±5 kΩ

Blunt (gold button) electrodes which do not penetrate the epidermis:

Range * 300–500 kΩ

Carbonized rubber patches accurately cut to 0.5 cm diameter:
Range * without electrode gel 500 kΩ–1 mΩ
Range * with electrode gel 300–600 kΩ

* after ear lobe has been cleaned with ethanolic solution.

Examples of application

For pain amelioration

Rats received specific electrical stimulus while restrained for periods of treatment varying between 5, 10, 20, 40, 60, 120 and 180 min. The response to an acute painful challenge comprising either noxious dry heat to the tail, noxious wet heat to the tall or an intraperitoneal injection of hypertonic saline was compared with that of rats sham-treated for the similar time period and with basal (time 0) treatment.

For amelioration of drug withdrawal

Rats were addicted to morphine by implantation of miniature pumps loaded with the drug for periods varying up to 14 days. The pumps were removed and 24 hr later the abstinence effects were compared in rats receiving electrostimulus with sham-treated animals.

For amelioration of the effects of stress

Rats receiving chronic restraint stress, in some instances after prior periods of isolation stress. The neurochemical response of electrostimulated and sham-treated rats are compared.

Once efficaceous signals (which ameliorate the noxious responses in the above 3 examples) have been identified, fresh groups of animals are subjected to that electrostimulus before humane sacrifice. After this time tissues are then assayed and the various hormonal effects associated with the efficaceous current identified by comparison of treated, sham-treated and basal (untreated and minimally-handled rats). The involvement of these neurohumoural substances is confirmed by determining the influence of prior administration of specific chemical antagonists to these neuro-hormones.

Efficaceous Currents

Packet size and pause time

At any specific frequency the optimal number of pulses per packet (ppp), and pause between succeeding packets (Dp), was determined by comparing the efficacy of the current administered at either 64, 128, 250, 500, 750, 1000, 1250, 1500, 1750, 2000, 2250, 2500 ppp with pauses (Dp) of 1, 2, 5, 10, 15, 20, 25, 50 and 100 sec between succeeding packets.

10 Hz Frequency

A prescription delivering 250 ppp and 10 sec Dp is efficaceous in providing pain relief characterized by a general feeling of drowsiness/euphoria. When prescription is administered with a Dp of 100 sec, the signal may be administered continuously (rather than for a given period of time e.g. 60 min) and is particularly efficaceous for pain control during the late evening and throughout the night. Both these 250 ppp prescriptions decrease ACTH levels while various endogenous opioids including $\beta$-endorphin (BE) are elevated in the blood.

A prescription comprising of 750 and 1000 ppp (750 providing a quantitatively greater effect for the majority of subjects) with Dp 10 sec is highly efficient as a broad range analgesic. It is especially efficaceous for inflammatory pain and where more than one type of diverse pain is present simultaneously.

This "750" prescription enhances mood and produces relaxation without drowsiness. This prescription is particularly efficaceous when administered at times when ACTH levels would be expected to be elevated, for example for people on a normal 12 h light:dark cycle, this would be the early morning, post lunch time or under conditions of extreme stress or anxiety, including the anxiety associated with chronic pain conditions. This 750 prescription decreases the turnover rate of the neurotransmitter noradrenaline for a given period. Its action may be prolonged by administering the signal in trains comprising 3 complete (with 10 sec pause) packets separated by 10 min "off" periods. Such a signal may be administered all day during the "awake period".

It is one of the most effective prescriptions for diminishing ACTH levels. The principal opiate-like effect of this prescription is on dynorphin although the magnitude and nature of this effect (on dynorphin) depends upon the time and duration for which the current is applied.

Both of these prescriptions should be applied at an amplitude of 10–12 $\mu$A under which conditions they may be used not only to control pain in the manner described an example 1 but also to assist persons habituated cigarette smoking to quit the habit, in which case the 250 ppp 10 sec prescription may also be applied at an amplitude of 30 $\mu$A.

The significance between these two prescriptions is that at 10–12 $\mu$A, both the 250 and especially the 750 ppp act by suppressing the neuronal punishment systems (see, e.g., White and Rumbold, Psychopharmacology (1988) 95: 1–14). The 750 ppp prescription inhibits the rate of noradrenaline and histamine turnover in the various brain regions, but stimulates histamine turnover in the adrenal glands where it is associated with the release of hormonal substances, principally corticosterone and opioid peptide fragments, which by feedback inhibition suppress the action of the central neurotransmitter associated with alarm or pain reactions.

Various "mixed" prescriptions e, g, an alternating 250 ppp and 750 ppp pulse packet separated by 10 s pauses (administered in a 60 min train) have been found to be particularly effective for treating inter alia pain in the head region such as trigeminal neuralgia and TMJ (temparo-mandibular joint pain), When however the 250 ppp prescription is delivered at an amplitude of 30 $\mu$A, the inhibition of the punishment systems is less evident and the efficacy of the signal owes more to a stimulation of the reward system of the brain (see e.g. Wise, Pharmac Ther. Vol 35 pp 227–263, 1987). This is evidenced by enhanced turnover of neuronal dopamine and elevated BE activity. The 250 ppp may be used at 10–12 or 30 $\mu$A to ameliorate the abstinence effects of withdrawal from other drugs of abuse, inhibition of the punishment systems is more important during the early treatment (detoxication) stages, whereas enhancing the reward system of the brain is of more benefit during the rehabilitation stage of treatment.

0.1 Hz frequency

The signal may be applied continuously (with no pauses) at 10–12 $\mu$A amplitude, 2.0msec positive pulse. At this frequency the signal may be used inter alia to promote sleep or hypnosis treatment.

2 Hz frequency

The signal should be administered at 200 or 1000 ppp with 10 sec Dp at 10–12 $\mu$A amplitude, 2.0msec positive pulse. Such a current may be administered inter alia to control pain by stimulating endogenous opioid activity but it is most efficaceous in withdrawal from opiate drugs of abuse as described in example 5. This is because the current stimulates the action of the endogenous opioids which have been down regulated by the abuse of the exogenous substances.

500 Hz frequency

Both 1000 ppp at 10 sec Dp and 250 ppp at 100 sec Dp are antinociceptive and are particularly effective for ameliorating pain mediated via spinal processes. Unlike the 10 Hz prescriptions for pain relief, these prescriptions should only be administered for periods of up to 60 min with at least 180 min intervals before a succeeding stimulus, and preferably only one a day. In the early stages of detoxication from the effects of alcohol abuse, the 1000 ppp, 10 Dp prescription is administered for 24 hr basis. These prescriptions increase serotonergic activity and also stimulate histamine turnover. They decrease the narcotic effects of both barbiturates and alcohol. These prescriptions are delivered at 10-12 $\mu$A with a 1.0 ms positive pulse duration setting.

2000 Hz frequency

Administered for short periods of up to 40 min in a continuous (no Dp) train this prescription prolongs the effect, for example on narcosis of hypnotic agents. This prescription may be used in the rehabilitation/detoxication of subjects abusing hallucinogenic agents such as LSD.

Ultra fast frequency

Prescriptions administered at a number of such frequencies, in particular 1.2 and 50 MHz stimulate the punishment centers of the neuronal systems. These prescriptions should be administered in packets lasting 100 sec interspersed with 10 sec for periods of not less than 20 or more than 40 min. The number of such cycles that may be applied to the recipient will depend upon the tolerance of the individual as the current does raise anxiety levels and can impair sleeping. Since these prescriptions stimulate both cholinergic activity and the level of ACTH release, these prescriptions could be of use in the treatment of conditions involving impairment of memory such as Alzheimer's disease. The effect of ACTH is the principal mechanism by which such prescriptions may also be used to help smokers cease the practice without experiencing abstinence effects but generally the method described in example 4 is more appropriate. The stimulatory effect of these currents on ACTM may also be used therapeutically to decrease the sleeping time post-operatively following the use of narcotic agents.

Examples to illustrate treatment

EXAMPLE 1

Treatment to ameliorate pain

A subject suffering from an inflammatory pain condition would be treated with a signal at 10-12 $\mu$A of positive pulse duration 2.0 msec. At 10Hz this would be delivered in packets of 750 ppp with 10 sec Dp for a period of 60 min between 10.00-12.00 h and 14.00-16.00 h daily until pain amelioration lasting >24 h is achieved (normally 4 or 5 days ). After this time the treatment may be diminished to once daily, then once every two days, thence on demand.

EXAMPLE 2

Chronic main coupled with drug withdrawal problems when the subject ceases to use habituating drugs The 750 ppp prescription described above may be used continuously after the subject awakens until (for most subjects on a 12 h light: dark cycle) 20.00h. The individual would then receive 2 h of the continuous 0.1 Hz prescription also at 10-12 $\mu$A and 2.0 msec positive pulse duration, followed immediately by a signal of equal amplitude and duration, but delivered at 250 ppp 10 sec Dp. This signal would be administered for I h with two hours breaks between 1 h periods of treatment. This prescription would continue until the individual awakens on the following day when the treatment would revert to the original 750 ppp prescription.

EXAMPLE 3

Chronic pain caused by lower back injury

A prescription delivered at 500 Hz at 10-12 $\mu$A amplitude and 1.0 msec positive pulse duration the first cycle comprising 1000 ppp with a 10 sec Dp alternating with a succeeding cycle 2500 ppp and 10 sec Dp the complete train should last no more than 60 min and there should be a 3 h pause before a succeeding train.

EXAMPLE 4

Amelioration of withdrawal effects in cigarette smokers who quit smoking

The minimal treatment to be administered is 60 min of a 200 ppp 10 sec Dp signal of amplitude 10-12 $\mu$A and positive pulse duration of 2.0 msec. This treatment should be administered in the morning (before noon) period. The success of the treatment in aiding people to quit smoking increases if further treatment is administered 6 h later than the first. Generally the longer the treatment period the subjects experience, the fewer (if any) abstinence effects are observed. Persons experiencing depressive symptoms should receive 40 min treatment with the same signal at 30 $\mu$A amplitude. This latter treatment should not be administered within 2 h of a previous treatment. This treatment to enable people to cease smoking should continue a minimum of to a maximum of 7 days. The treatment should be administered with the appropriate behavioural modification therapy.

EXAMPLE 5

Amelioration of abstinence symptoms during withdrawal of drugs of abuse (including alcohol) of addicted subjects This may be achieved by administering a prescription which enhances the neurochemical reward systems e.g. 250 ppp, 10 sec Dp, 2.0msec positive pulse at 30 $\mu$A amplitude, or inhibits the neurochemical punishment system e.g. 750 ppp, 10 sac Dp, 2.0 msec positive pulse at 10-12 $\mu$A amplitude. Whichever of these prescriptions is applied, the treatment should still only be administered for i h in the morning and 1 h in the afternoon period. In between these treatments and up until 20.00h, the subject should receive trains of the 750 ppp prescription consisting of three packets separated by a 10 min train pause. After 20.00h the subject may be maintained during the sleep phase with either a 250 ppp, 100sec Dp, 2.0msec positive pulse duration, 10 Mr, 10-12 $\mu$A amplitude or a continuous 0.1Hz prescription of positive pulse duration 2.0msec and 10-12 µA amplitude.

The period that the treatments are administered will depend upon the stage of withdrawal from drugs of the subject and the quantity (and duration of abuse). This treatment represents the detoxication phase which would normally be expected to last no more than 3-5 days the recipient should be available for psychotherapy/counselling at the end of this phase. Thereafter the subject should receive a further 7-10 days of a prescription delivered at 2 Hz, 200 ppp, Dp, 2.0msec positive pulse duration at an amplitude of 10-12 µA. This prescription should be administered for 60min periods alternating with 60 min periods when no treatment is applied. After 7 days this treatment should be scaled down so that the subject receives no more than 2 treatments per day. 14 days after beginning the original treatment, the subject should not exhibit any abstinence symptoms i f no treatment is administered at all. This latter prescription may be administered on a no more than twice a day basis to aid in the psychological rehabilitation process over the succeeding months however.

In the case of detoxication from heroin or other opiate addictions, a prescription delivered at 133 Hz, 10-12 µA amplitude, 2.0msec positive pulse duration comprising packets of 2500 ppp and 10 sec Dp is particularly effective during the daylight hours.

In the case of alcohol abuse a 500 Hz prescription comprising 1000 ppp, 10 sec Dp with positive pulse duration 1.0 msec of amplitude 10-12 µA is effective in the detoxication stage but should be administered during the light period of the day only. If the subject is unable to sleep they may be treated at night in the manner described above for the other chemical addictions.

Other applications

From knowledge of the action of TCET on various neurohumoural processes it is reasonable to assume that the treatment could be beneficially applied to other medical problems including:

1. Immune dysfunction

By controlling corticosteroid levels by modulating ACTH release from the pituitary, lowering the concentration of blood dynorphin and adrenal histamine, the autoimmune defence mechanisms responsible for the inflammatory reactions in conditions like rheumatoid arthritis could be controlled, with the appropriate prescription.

2. Parkinson's disease

In the early stages of this condition, the dopaminergic activity of central neural system is enhanced by TCET.

3. Alzheimer's disease

There is evidence that the cholinergic activity in the frontal lobes is increased by the appropriate prescription. It therefore follows that as with Parkinson's disease, provided that the tissues to be treated have not deteriorated excessively (i.e. in the early stages of the condition) it is likely that TCET could retard the deterioration of the neurons by boosting the activity of the appropriate neurotransmitters.

4. Depression

Marked enhancements of mood have been observed when treating subjects with some prescriptions to alleviate pain. Since these prescriptions modulate the tone of neurotransmitters associated with behavior, and the level and release of ACTH may also be suppressed with the appropriate prescription, it is reasonable to assume that TCET would be efficaceous for the treatment of various forms of depression.

5. Insomnia/Jet lag

TCET has been demonstrated to decrease the secretion of ACTH in both experimental and clinical conditions, and this neurohormone is concerned inter alia with the process of awakening. It is probable that suppression of this hormone will aid the sleep process, especially if coupled with prescriptions which reduce anxiety by lowering noradrenergic tone. It also follows that supression of this substance at specific times of day could help offset the shift in diurnal/circadian rhythm "jet-lag" associated with travel between time zones.

6. Stress/anxiety phobias

Some prescriptions have an anti-anxiety component in the mode of action in ameliorating pain and when suppressing noradrenaline turnover, some prescriptions have also enabled habituated subjects to cease using anxiolytic substances. It therefore follows that such prescriptions could be used to replace anxiolytic drugs for the control of stress/anxiety situations. It is also possible that such treatment would be beneficial for subjects suffering from behavioural abnormalities such as schizophrenia.

7. Neurological dysfunction

Enhancement of the release of neurotransmitters involved in motor control could be beneficial in various conditions such as epilepsy, muscular sclerosis, muscular dystrophy, etc.

8. Appetite disturbance

Stimulating the secretion of various opioid peptides while inhibiting other peptidergic substances such as ACTH and cholecystokinin (CCK) could be used to stimulate appetite in individuals suffering from anorexia nervosa. Conversely inhibiting opioid peptides should suppress appetite in individuals who overeat. It therefore follows that TCET administered at the appropriate time of day could be used to suppress or enhance appetite.

9. Sexual dysfunction

In some cases of erectile impotence TCET could be used to stimulate the parasympathetic, while inhibiting the sympathetic nervous system.

Similarly, amenorrhea/dysmenorrhea with origins in stress and concomitantly elevated prolactin secretion may be attenuated by stimulating dopaminergic and opioid pathways at specific intervals in the menstrual cycle so regulating menses.

10. Anaesthesia adjunct

Some prescriptions increase and others diminish the effects of an acute dose of hypnotic substances. Therefore TCET introduced post-operatively for pain control could also lower the amount of anaesthetic necessary to maintain the patient during operations and thence enable the patient to rapidly recover from the anaesthetic post-operatively as well as controlling post operative pain.

11. Detoxication

A side-effect of TCET is the stimulation of hepatic function as the result of increased hypothamo-pituitary activity. This can be useful for the clearance of drugs and toxic substances from the individual and could also be useful to protect kidney function in the case of deliberate acute drug overdose.

Detailed description of ear clip electrode

According to one aspect, the present invention provides a bifurcated electrode assembly comprising two arms between which an ear or other fleshy body part can be gripped; Biasing means, such as a threaded screw, arranged for biasing the two arms together so as to grip the ear etc., a threaded electrode carrier being mounted in a passage of one of the arms for advancement towards to ear. Preferably locking means are provided for locking the electrode carrier against rotation. The electrode carrier preferably has a threaded split collet with a blind hole in which an electrode needle can be gripped. Alternatively, the electrode needle can be permanently mounted in the carrier, e.g. by being molded in situ.

According to another aspect, the invention provides a head support device for supporting a pair of electrode assemblies, comprising a resilient wire or the like having a U-shaped portion shaped to fit from the tops of the ears round the nape of the neck, and a pair of end portions shaped to descend generally vertically from the top front of the ears and to each of which an electrode assembly can be attached.

The electrode assembly preferably includes a pivoted bracket for attachment to the head support device.

These and other significant features of the invention will become apparent from the following description of a skin electrode mounting system embodying the invention, given by way of example, with reference to the drawings:

FIG. 1 is a general view of an electrode assembly 10. A base portion 1 has two major arms 12 and 13 extending from it, forming a pair of jaws to be placed around the lobe or other desired part of the ear. A bolt 14 is mounted in arm 12 and engages in a threaded hole in the arm 13, so that by turning its head 15, the arms 12 and 13 can be moved together to grip the chosen part of the ear. The facing parts of the ends of the arms 12 and 13 are grooved or serrated to give a good grip. The natural positions of the arms 12 and 13 may be sufficiently divergent that the gap between their outer ends is wider than the maximum thickness of the ear. Alternatively, the arms 12 and 13 may be formed so that in their natural or unstressed condition, the gap between their ends is that of a typical ear lobe. I f that is so, the screw 14 must be able to pull the arms together and force them apart. This can be achieved by providing the screw 14 with a collar (not shown) attached to it adjacent to the inner side of the arm 12.

An electrode carrier 16 is mounted in a threaded hole towards the end of arm 12. The hole is deepened by a collar 17. As shown in FIGS. 2 and 3, the assembly 10 can comprise a single plastic molding which is bent in two by virtue of a narrower flexible middle section 18.

The electrode carrier 16 is illustrated in FIG. 4. It comprises a short, relatively thick screw having a knurled or ribbed head 19 and an axially mounted electrode needle 20 having a pointed end 21 and a distal end 22 onto which an electric lead can be connected by a crimped ferrule connector or the like. Optionally, carrier 16 can be fitted with a locking nut (not shown) to prevent rotation. Also, calibration can be provided, so that the same degree of advancement of the needle 20 can be achieved on different occasions.

Figure 7:
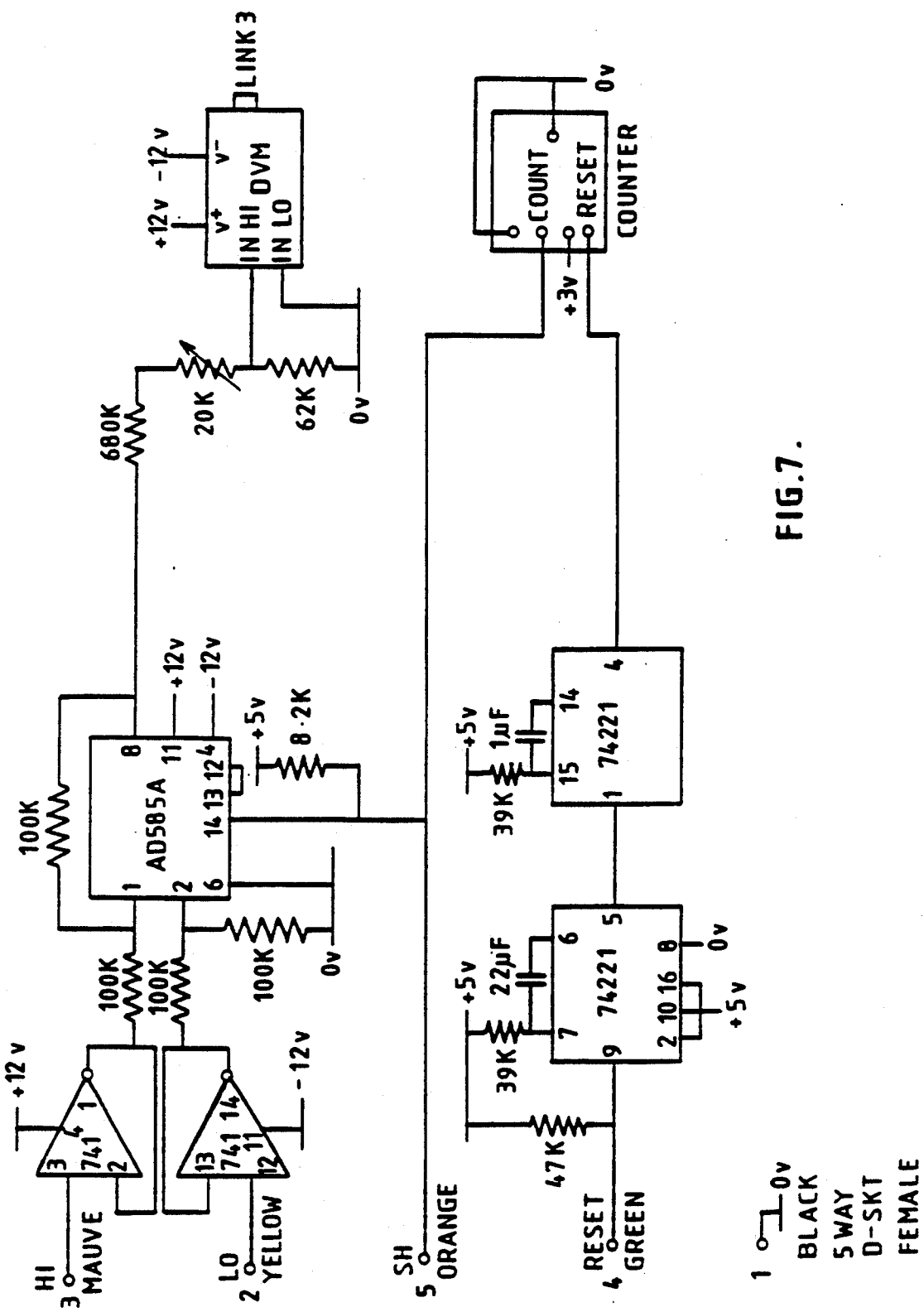

Apparatus for generating a suitable signal is described, for example, in International Patent Application No. WO 86/02567. Alternatively, a power supply circuit and signal generator are shown in FIGS. 5 to 7.

We claim:

1. An electrode for providing TCET, comprising:
an electrical conductor for application to an ear of a patient, connected to a lead for supplying a TCET signal from a signal generating device, the conductor comprises a generally conical needle point capable of only penetrating the epidermis, so as to provide good electrical contact over a very small area of the epidermis; and
means on the conductor for controlling the pressure at which the needle point penetrates into the epidermis.

2. An electrode according to claim 1, including means adapted to provide an overall impedance of less than 10 kΩ when connected to the ear of a patient so as to complete a circuit with the cranium in an operating TCET arrangement.

3. An electrode according to claim 2, wherein the means is adapted to provide an impedance of about 65–90 kΩ or 25–35 kΩ.

4. Apparatus for use in TCET comprising means for generating an electric signal at a current of less than 200 μA (0.2 mA), operatively connected to an electrode according to claim 1.

5. Apparatus according to claim 4, wherein said means is adapted to provide a current of 1 to 30 μA.

6. Apparatus according to claim 5, wherein said means is adapted to provide a current of 5 to 20 μA.

7. Apparatus according to claim 6, wherein said means is adapted to provide a current of 10–15 μA.

8. An electrode for providing TCET, comprising:
an ear clip comprising a bifurcated or generally U-shaped holder capable of being located around an ear lobe or other desired part of the ear;
an electrical conductor mounted on the holder, in the form of a conically pointed electrode needle arranged to press against the ear part located between arms of the U-shaped clip to only penetrate outer layers of the skin, so as to provide good electrical contact over a very small area of the skin;
adjustable means on the electrode needle for controlling the pressure at which the point of the electrode needle presses into the outer layers of the skin; and
means provided on the electrode needle for electrical connection to a lead for supplying a TCET signal from a signal generator.

9. An apparatus for use in TCET, comprising:
an electrical conductor for application to skin of a patient, the conductor being connected to a lead for supplying a TCET signal from a signal generating device, the conductor comprising a generally conical needle point capable of only penetrating an epidermis layer of the skin, so as to provide good electrical contact over a very small area of the epidermis;
means for generating an electric signal at a current of 200 μA (0.2 mA) operatively connected to the lead, wherein said means is adapted to provide an AC signal in which each positive pulse is relatively short and high without being spiked and the following negative pulse is relatively wide and low, the total amount of positive and negative charge being balanced.

10. Apparatus according to claim 9, wherein said means is adapted to provide a signal in which each negative pulse is 5–10 times as wide as the positive pulse.

11. An apparatus for use in TCET, comprising:
an electrical conductor for application to sin of a patient, the conductor being connected to a lead for supplying a TCET signal from a signal generating device, the conductor comprising a generally conical needle point capable of only penetrating an epidermis layer of the sin, so as to provide good electrical contact over a very small area of the epidermis;

means for generating an electric signal at a current of 200 μA (0.2 mA) operatively connected to the lead, wherein said means is adapted to provide a prescription signal selected from:

(1) 9-13 Hz in packets of 200-300 pulses separated by pauses of 9-11 seconds, in trains of 60 minutes maximum separated by rests of at least 3 hours, at a current of 28-32 μA or 10-15 μA;

(2) 9-13 Hz in packets of 70-800 pulses separated b pauses of 9-11 seconds, in trains of 60 minutes maximum separated by rests of at least 3 hours, at a current of 10-15 μA;

(3) 9-13 Hz in packets of 200-300 pulses separated b pauses of about 100 seconds, in trains of 60 minutes maximum separated by rests of at least 3 hours, at a current of 28-32 μA or 10-15 μA;

(4) 9-13 Hz in packets of 700-800 pulses and some of 200-300 pulses separated by pauses of 9-11 seconds, in trains of 60 minutes maximum separated by tests of at least 3 hours, at a current of 28-32 μA or 10-15 μA;

(5) about 2 Hz in packets of about 200 pulses or about 1000 pauses separated by pauses of 9-11 seconds, at 10-12 μA in one continuous train;

(6) about 500 Hz in packets of about 1000 pulses with 9-11 second pauses of 200-300 pulses with about 100 second pauses at 10-15 μA in trains of 60 minutes maximum separated by rests of 3-23 hours;

(7) about 0.1 Hz at 10-12 μA with no pauses or rests;

(8) about 2000 Hz continuously for up to 40 minutes at 10-15 μA; and (9) about 1.2 or about 50 MHz in packets of about 100 seconds with 10 second pauses, in trains of 20-40 minutes.

12. Apparatus according to claim 11, wherein said means is adapted to provide a prescriptive signal selected from (1) to (5), (7) and (9) with a positive pulse width of about 2 milliseconds.

13. A method of providing TCET to a patient, comprising the steps of:

applying percutaneous electrodes having conical needle points to a head of the patient, such that the needle points only penetrate the epidermis, so as to provide good electrical contact over a very small area of the epidermis; and applying a series of electric signals of defined amplitude and duration to said electrodes to supply a TCET signal across the head of the patient by means of said percutaneous electrodes.

14. In a method of providing TCET to a patient according to claim 13, further comprising generating the series of signals at a current of less than 200 μA (0.2 mA).

* * * * *